(12) United States Patent
Harden et al.

(10) Patent No.: US 9,390,898 B1
(45) Date of Patent: Jul. 12, 2016

(54) SYSTEM AND METHOD FOR FUSING CHEMICAL DETECTORS

(71) Applicant: Leidos, Inc., Reston, VA (US)

(72) Inventors: Charles Stephen Harden, Bel Air, MD (US); Robert James Schafer, Port Deposit, MD (US)

(73) Assignee: Leidos, Inc., Reston, VA (US)

( * ) Notice: Subject to any disclaimer, the term of this patent is extended or adjusted under 35 U.S.C. 154(b) by 51 days.

(21) Appl. No.: 14/474,559

(22) Filed: Sep. 2, 2014

Related U.S. Application Data

(60) Provisional application No. 61/871,927, filed on Aug. 30, 2013.

(51) Int. Cl.
  *H01J 49/00* (2006.01)
  *H01J 49/02* (2006.01)
  *G01N 27/62* (2006.01)
  *H01J 49/40* (2006.01)

(52) U.S. Cl.
  CPC .......... *H01J 49/0095* (2013.01); *G01N 27/622* (2013.01); *G01N 27/624* (2013.01); *H01J 49/004* (2013.01); *H01J 49/005* (2013.01); *H01J 49/009* (2013.01); *H01J 49/0013* (2013.01); *H01J 49/0022* (2013.01); *H01J 49/40* (2013.01)

(58) Field of Classification Search
  None
  See application file for complete search history.

(56) References Cited

U.S. PATENT DOCUMENTS

| | | | | |
|---|---|---|---|---|
| 2,422,264 A * | 6/1947 | Seaman | | H01J 49/26 250/281 |
| 4,266,127 A * | 5/1981 | Chang | | H01J 49/145 250/281 |
| 4,445,038 A * | 4/1984 | Spangler | | G01N 27/622 250/287 |
| 5,227,628 A * | 7/1993 | Turner | | G01N 27/66 250/282 |
| 5,543,331 A * | 8/1996 | Puumalainen | | G01N 27/66 250/382 |
| 6,239,428 B1 * | 5/2001 | Kunz | | G01N 27/622 250/282 |
| 6,459,079 B1 * | 10/2002 | Machlinski | | G01N 27/622 250/286 |
| 6,627,878 B1 * | 9/2003 | Machlinski | | G01N 1/2202 250/286 |
| 6,815,671 B2 * | 11/2004 | Johnston | | G01N 27/622 250/287 |
| 7,119,328 B2 * | 10/2006 | Kaufman | | G01N 27/624 250/281 |
| 7,259,369 B2 * | 8/2007 | Scott | | G01N 27/622 250/281 |
| 7,576,321 B2 * | 8/2009 | Wu | | G01N 27/622 250/281 |
| 7,649,170 B2 * | 1/2010 | Wang | | H01J 49/0095 250/281 |
| 7,714,284 B2 * | 5/2010 | Miller | | G01N 27/624 250/282 |
| 8,288,718 B2 * | 10/2012 | Li | | G01N 27/622 250/281 |
| 8,309,913 B2 * | 11/2012 | Wang | | H01J 49/40 250/281 |
| 8,754,366 B2 * | 6/2014 | Burchfield | | G01N 27/624 250/283 |
| 2003/0034449 A1 * | 2/2003 | Miller | | H01J 49/42 250/287 |
| 2003/0089847 A1 * | 5/2003 | Guevremont | | G01N 27/624 250/282 |

(Continued)

OTHER PUBLICATIONS

G.A. Eiceman and Z. Karpas, "Ion Mobility Spectrometry, $2^{nd}$ Edition," CRC Press Taylor & Francies Group, Boca Raton, FL (2005).
E. Nazarov, et al., "Miniature DMS-IMS Detector for Enhanced Resolving Power," $16^{th}$ International Conference on Ion Mobility Spectrometry, Mikkeli, Finland, Jul. 2007.
A. G. Anderson, et al., "DMS-IMS2, GC-DMS, DMS-MS: DMS Hybrid Devices Combining Orthogonal Principles of Separation for Challenging Applications," Chemical, Biological, Radiological, Nuclear, and Explosives (CBRNE) Sensing IX, Edited by A. W. Fountain, P. J. Gardner, Proceedings of the SPIE, vol. 6954, pp. 69540H-69540H-12 (2008).

*Primary Examiner* — Michael Logie
(74) *Attorney, Agent, or Firm* — Dawn-Marie Bey; Bey & Cotropia PLLC

(57) ABSTRACT

Two complementary approaches to the science of IMS technology, IMS and differential IMS (DIMS), are combined into a single instrument to provide improvements in interference rejection without sacrificing detection sensitivity. The technology is applicable to, inter alia, the analysis of trace quantities of toxic or otherwise dangerous organic chemical materials. The approach improves both sensitivity and specificity (interference rejection) of field detection instrumentation.

13 Claims, 17 Drawing Sheets

(56) References Cited

U.S. PATENT DOCUMENTS

| | | | |
|---|---|---|---|
| 2005/0040330 A1* | 2/2005 | Kaufman | G01N 27/624 250/293 |
| 2005/0173629 A1* | 8/2005 | Miller | G01N 27/624 250/290 |
| 2005/0199799 A1* | 9/2005 | Takada | H01J 49/0095 250/288 |
| 2005/0230615 A1* | 10/2005 | Furutani | B82Y 10/00 250/287 |
| 2005/0253061 A1* | 11/2005 | Cameron | G01N 27/624 250/287 |
| 2006/0192103 A1* | 8/2006 | Landgraf | H01J 49/40 250/287 |
| 2006/0289747 A1* | 12/2006 | Schultz | G01N 27/622 250/294 |
| 2007/0176092 A1* | 8/2007 | Miller | H01J 49/004 250/288 |
| 2007/0277589 A1* | 12/2007 | Harden | G01N 27/622 73/31.03 |
| 2008/0149824 A1* | 6/2008 | Miller | G01N 27/624 250/287 |
| 2008/0296493 A1* | 12/2008 | Willoughby | H01J 49/062 250/288 |
| 2009/0090853 A1* | 4/2009 | Schoen | H01J 49/06 250/282 |
| 2009/0189064 A1* | 7/2009 | Miller | G01N 30/7206 250/282 |
| 2010/0001182 A1* | 1/2010 | Burchfield | G01N 27/624 250/283 |
| 2010/0314548 A1* | 12/2010 | Munchmeyer | G01N 27/624 250/375 |
| 2011/0068264 A1* | 3/2011 | Xu | G01N 27/622 250/286 |
| 2011/0183431 A1* | 7/2011 | Covey | G01N 27/624 436/173 |
| 2014/0339416 A1* | 11/2014 | Vidal-de-Miguel | H01J 49/004 250/282 |
| 2015/0076342 A1* | 3/2015 | Campbell | H01J 49/165 250/288 |
| 2015/0233866 A1* | 8/2015 | Verenchikov | G01N 27/622 250/282 |

\* cited by examiner

Fig. 1: Linear Electric Field IMS
PRIOR ART

Fig. 2: Non-Linear, RF-DC Electric Field, DIMS
PRIOR ART

Fig. 3: Spectra resolution vs. size of analyte ions.
PRIOR ART

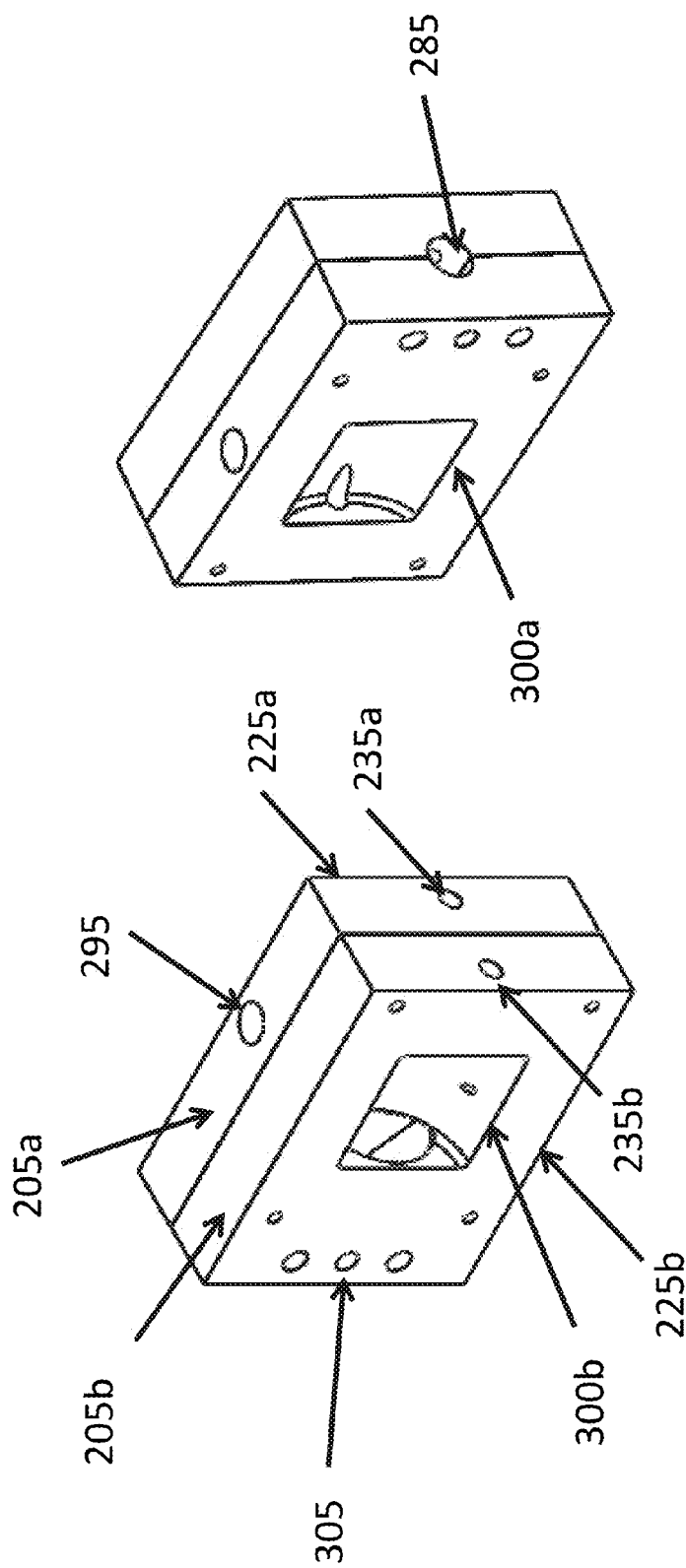

SYSTEM AND METHOD FOR FUSING CHEMICAL DETECTORS

CROSS-REFERENCE TO RELATED APPLICATIONS

The present application claims the benefit of priority to similarly titled U.S. Provisional Patent Application Ser. No. 61/871,927 filed Aug. 30, 2014, the contents of which is incorporated herein by reference in its entirety.

BACKGROUND OF THE EMBODIMENTS

1. Field of the Embodiments

The embodiments are generally directed to chemical detectors and more particularly to an improved chemical detector which fuses previously independent approaches to ion mobility spectrometry (IMS) into a single detector.

2. Description of Related Art

Ion Mobility Spectrometry (IMS) has been the primary technology for chemical warfare agent detection for at least 30 years. Screening of airport passengers for explosives and illegal drugs has relied on IMS for about the same period. There are hundreds of thousands ion mobility spectrometers in use throughout the world. Instrumentation advantages in terms of small size and low electrical power requirements coupled with excellent sensitivity and spectrometric specificity make IMS an ideal technology for field detectors. As with any analytical chemistry technique, improved sensitivity and specificity without sacrificing size, weight, power and cost benefits are continually sought. The number one complaint by users of IMS instrumentation is that the systems are prone to interferences. As requirements for field detection of various and "non-traditional" substances increase, complaints of interferences are likely to increase.

Ion Mobility Spectrometry (IMS) is the study of the motion of gas-phase ions under influence of electric fields. Several methods for study on the ion motion are used throughout the IMS field. A combination or "fusion" of two of these methods is proposed—the IMS methods will be referred to here as "Linear" IMS or just IMS (the traditional term) and "Differential" IMS or DIMS. A detailed treatment of theory and practice of IMS can be found in the book "Ion Mobility Spectrometry—$2^{nd}$ Edition" by G. A. Eiceman and Z. Karpas, CRC Press Taylor & Francis Group, Boca Raton (2005). The substance of this reference is considered to be known to those having skill in the present art and is incorporated herein by reference.

Currently, existing field detectors use either IMS or DIMS, but not both. For example, the LCD 3.3 (Light Weight Chemical Detector) from Smiths Detection uses IMS processing. While the JUNO detector developed by Chemring Detection Systems is exemplary of a previously proposed detector that uses DIMS processing for detection of CWA and low vapor pressure agents.

There is no literature record of IMS and DIMS sensor and data fusion where the two complementary technologies have been operated in parallel. There have been previous attempts to fuse IMS and DIMS technologies as described in E. Nazarov, et al.; "Miniature DMS-IMS Detector for Enhanced Resolving Power;" 16th International Conference on Ion Mobility Spectrometry, Mikkeli, Finland; July 2007 and in A. G. Anderson, et al; "DMS-IMS2, GC-DMS, DMS-MS: DMS hybrid devices combining orthogonal principles of separation for challenging applications;" Chemical, Biological, Radiological, Nuclear, and Explosives (CBRNE) Sensing IX. Edited by A. W. Fountain, P. J Gardner; Proceedings of the SPIE, Volume 6954, pp. 69540H-69540H-12 (2008). The described approach used a DIMS device for rapid separation of target ions and introduction of separated ions into two IMS instruments. A DIMS device separates positive and negative ions simultaneously. Positively charged ions are directed into an IMS device which is appropriately biased and negative ions are directed into the other IMS device. While this design, theoretically, provides for enhanced separation of analyte ions—such is not necessarily the case. Referring to FIG. 3 it can be seen that if the DIMS device selects small ions for analysis by the IMS systems, no resolution is gained since IMS cannot effectively separate small ions. For large ions there is little to no separation by the DIMS system, the IMS system is relied on to separate the ions. In both cases, sensitivity is sacrificed due to ion loses between the mobility spectrometers with insignificant improvements in resolution.

SUMMARY OF THE EMBODIMENTS

The present embodiments combine or "fuse" two complementary approaches to the science of IMS technology into a single instrument to provide improvements in interference rejection without sacrificing detection sensitivity. The two techniques are referred to as IMS and differential IMS (DIMS). The technology is applicable to, inter alia, the analysis of trace quantities of toxic or otherwise dangerous organic chemical materials. The approach described herein improves both sensitivity and specificity (interference rejection) of field detection instrumentation.

The embodiments combine the two techniques into a single instrument and combine the data outputs of the two technologies through the use of advanced signal processing techniques to take advantage of the complementary nature of the two approaches. The combination is such that each IMS technique processes an ingested sample independently, i.e., in parallel, and then the data is combined to give a single result with excellent sensitivity and interference rejection.

More particularly, in a first exemplary embodiment, a chemical agent detector includes: an ionization chamber including at least one ion source for generating positive and negative ions from a sample; a first ion mobility spectrometry cell integrated with the ionization chamber for receiving at least a first portion of the positive ions therefrom; a second ion mobility spectrometry cell integrated with the ionization chamber for receiving at least a first portion of the negative ions therefrom; a differential ion mobility spectrometry cell integrated with the ionization chamber for receiving at least a second portion of the positive ions and at least a second portion of the negative ions therefrom; and a processor for separately receiving first detection data from the first ion mobility spectrometry cell, second data from the second ion mobility spectrometry cell, and third data from the differential ion mobility spectrometry cell and processing the first, second and third detection data to determine presence of one or more chemical agents in the sample.

In a second exemplary embodiment, a process for parallel chemical agent detection includes: introducing a sample into an ionization chamber; ionizing the sample to create positive and negative ions; receiving at a first end of a first ion mobility spectrometry cell from the ionization chamber at least a portion of the positive ions; receiving at a first end of a second ion mobility spectrometry cell from the ionization chamber at least a portion of the negative ions; introducing a drift gas into a second end of each of the first and second ion mobility spectrometry cells, wherein the drift gas flows in an opposite direction from a flow of the portions of positive and negative ions in the first and second ion mobility spectrometry cells; receiving at a first end of a differential ion mobility spectrometry cell a second portion of each of the positive and negative ions from the ionization chamber and a first portion of the drift gas, wherein the first portion of the drift gas and the second portion of each of the positive and negative ions flow in the same direction within the differential ion mobility spectrometry cell; generating first and second chemical agent detection data at first and second detectors located at the second end of each of the first and second ion mobility spectrometry cells; generating third chemical agent detection data at a third detector associated with the differential ion mobility spectrometry cell; processing by a processing system the first, second and third chemical agent detection data determine presence of one or more chemical agents in the sample.

In a third exemplary embodiment, a hand-held chemical agent detector includes: an ionization chamber including at least one ion source for generating positive and negative ions from a sample, wherein the dimensions of the ionization chamber are less than 1 cm width, 2.5 cm length and 2.0 cm height; a first and second ion mobility spectrometry cells integrated with the ionization chamber for receiving at least a first portion of the positive and negative ions therefrom, wherein the dimensions of the first and second ion mobility spectrometry cells are less than 2.5 cm width, 2.0 cm length and 2.5 cm height; and a differential ion mobility spectrometry cell integrated with the ionization chamber for receiving at least a second portion of the positive ions and at least a second portion of the negative ions therefrom, wherein the dimensions of the differential ion mobility spectrometry cell are less than 1 cm width, 1.0 cm length and 3.0 cm height.

BRIEF DESCRIPTION OF THE FIGURES

The Summary of the Embodiments, as well as the following Detailed Description, is best understood when read in conjunction with the following exemplary drawings:

FIGS. 10a and 10b are isometric views of a first exemplary ionization chamber for use in the IMSx2 system described herein.

DETAILED DESCRIPTION

With regard to IMS, the terminal velocity of an ion drifting under the influence of the electric field is proportional to the electric field strength;

$$v_d = KE \qquad (1)$$

where $v_d$ is the ion's terminal velocity, E is the electric field strength and the proportionality constant, K, is defined as ion mobility. IMS is the traditional term used for linear field dependence IMS—this terminology will continue here.

Most ion mobility spectrometers are governed by Equation (1) which is an excellent approximation at relatively low electric field strengths, from zero to a few hundred volts per cm. At high electric field strengths upwards of a few kilovolts per cm, ion mobility cannot be represented as a constant value—ion mobility, K, takes the form $$K(E/N) = K(0)[1 + \alpha(E/N)] \qquad (2)$$

where $K(0)$ is the ion mobility under zero (and low) field conditions and E/N is the electric field normalized for pressure—the coefficient $\alpha$ is used to describe the dependence of ion mobility on high electric fields. To differentiate field-dependent ion mobility spectrometry from the more traditional linear ion mobility spectrometry the term Differential Ion Mobility Spectrometry or DIMS is used to indicate that ion mobility is variable with electric field strength. It should be noted DIMS is sometimes referenced by other names including Field Asymmetric Ion Mobility Spectrometry (FAIMS) and Field Ion Spectrometry (FIS). DIMS is the term used herein.

It is electric field dependence and the bases of operation that stimulated the idea for development of the embodiments described herein. IMS operates using DC electric fields and DIMS operates using a combination of RF and DC electric fields. Differences in separation of atmospheric pressure ions are significant. Although the techniques are not orthogonal in the strict sense, they are such that the fusion of ion mobility spectra will result in signal attributes that will enhance false alarm reduction and, in some cases, eliminate false alarms altogether.

Figure 1:
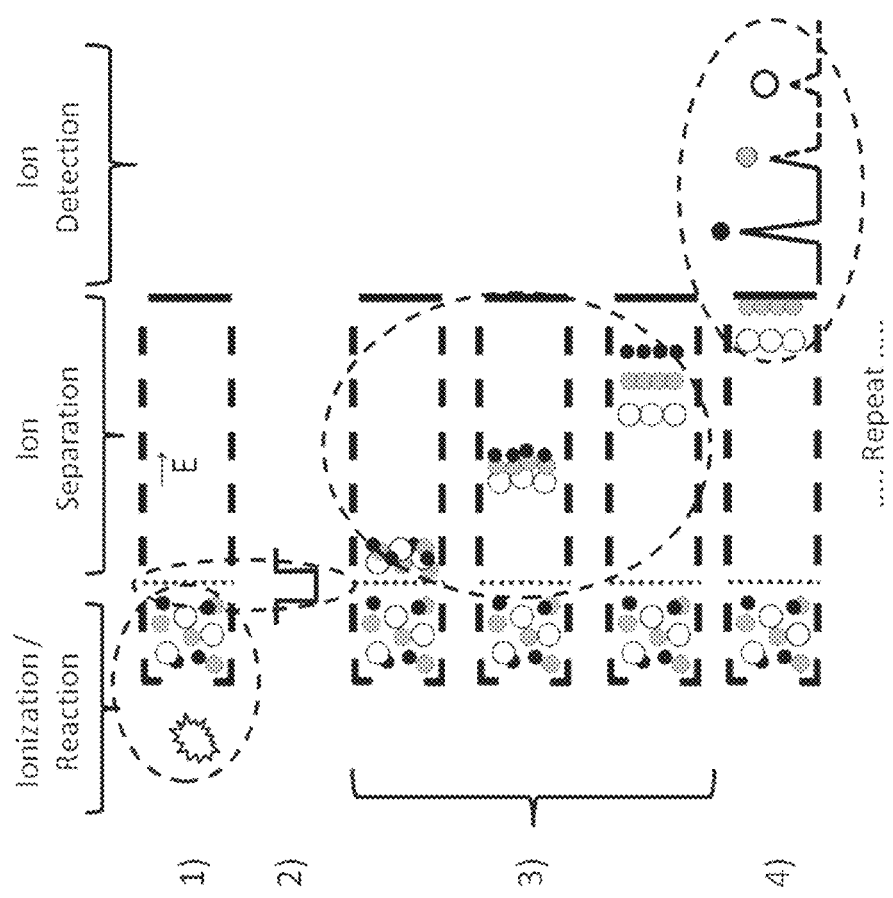
FIG. 1 is a prior art schematic showing separation of ions in an IMS system.

Following FIG. 1 from upper left to upper center down to lower center and finally to lower right the sequence of events is as follows: (1) "primary" ions are formed as a result of electric discharge or ionizing radiation, primary ions react with neutral species (target analytes) to form analyte ions and these ions drift into a reaction region where they are "trapped" by a grid that is electrically biased to prevent ions from passing through; (2) periodically the grid voltage is lowered for a short period (typically one to two hundred microseconds) which allows a packet of ions to enter the separation or drift region; (3) this packet of moves through the drift region under the influence of a constant electric field, E, where separation occurs according to the size of the ions and the charge on the ions—the smaller ions move faster than the larger ions; (4) as ions impact an ion collector a current is created in external circuitry and the variation of the ion current with "drift time" is an ion mobility spectrum—typically the spectrum drift time is 15-50 microseconds. This sequence is repeated as required by the application.

Figure 2:
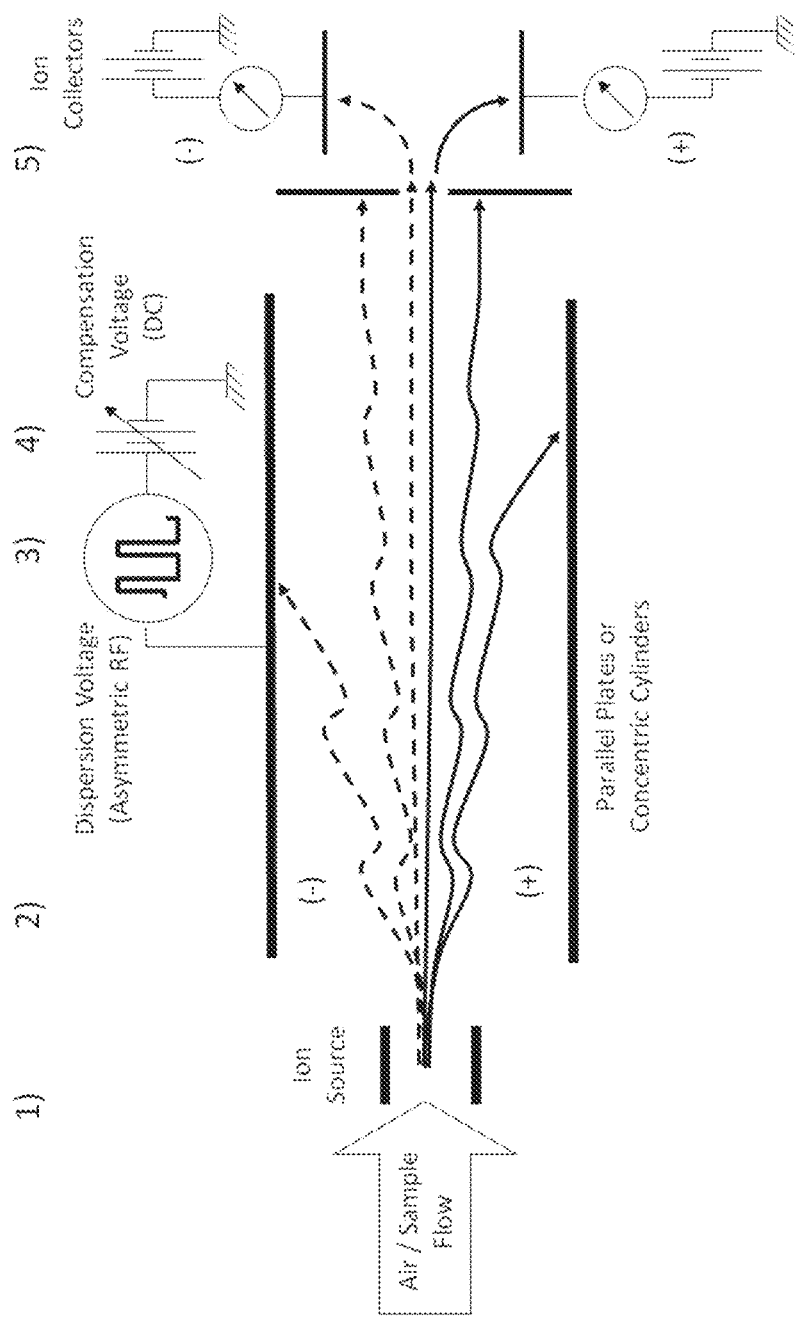
FIG. 2 is a prior art schematic showing separation of ions in a DIMS system.

From left to right in FIG. 2: (1) analyte laden air flows through a source of ionization, usually radioactivity, producing primary ions; reactions between primary ions and neutral analyte molecules are identical with the reactions in IMS; (2) ions continue to flow between a set of closely spaced (<1 mm) parallel plates or concentric cylinders; (3) as the ions flow between the plates they are subjected to an asymmetric RF field, the dispersion field, that varies at constant frequency, positively and negatively up to several kilovolts per cm wherein the high voltage part of the RF cycle is twice the amplitude and half the period of the low voltage part; (4) the RF field is superimposed on a DC voltage that is scanned over a few 10's of volts positively and negatively; (3,4) at a unique combination of RF dispersion voltage and DC compensation voltage an ionic species of a specific size and charge has a stable flight path through the plates, others impact walls and are neutralized—as the DC voltage is scanned other ions come into stability; (5) the stable ions are then directed into ion collectors that are biased to receive appropriately charged ions to create spectra, differential ion mobility spectra. The peak amplitude of the RF voltage is varied and another spectrum is obtained.

Figure 3:
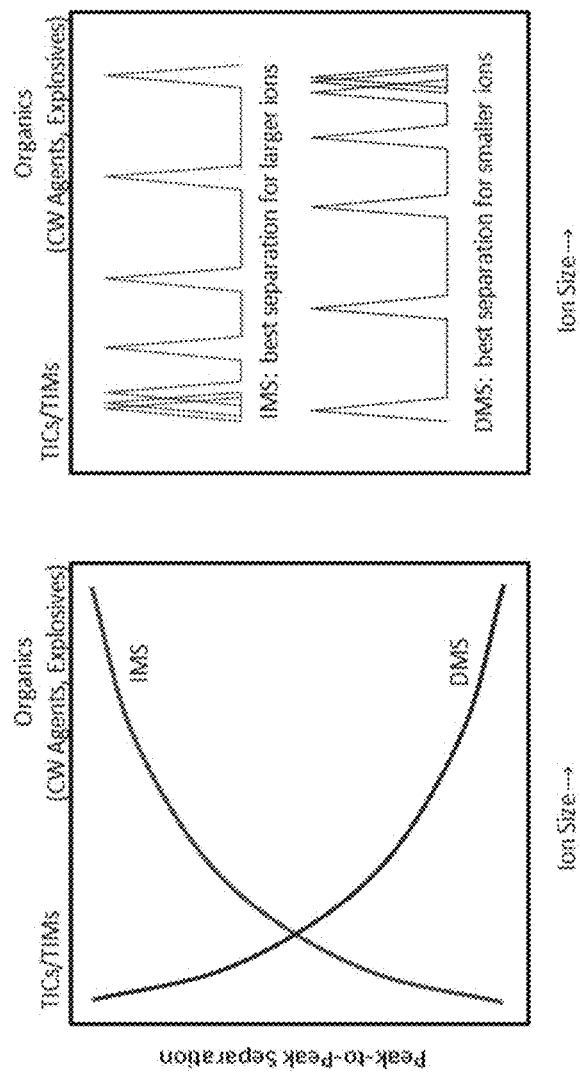
FIG. 3 illustrates that ion separation or spectral resolution of IMS and DIMS is dependent on the size of analyte ions.

Experiment has shown that ion separation or spectral resolution of IMS and DIMS is dependent on the size of analyte ions. FIG. 3 illustrates this point. The left hand side of FIG. 3 indicates that as the size of an analyte ion increases, separation of IMS analyte ion peaks increases while DIMS exhibits the opposite relationship. The right hand side of FIG. 3 is another representation of this characteristic—large ions tend to toward more overlap in DIMS, small ions tend to toward more overlap in IMS. Resolution can be adjusted through variation of electric fields, total drift voltage in IMS and RF voltage amplitude in DIMS. Reagent ion intensity, gate pulse width and repetition rate, length and spacing of DIMS electrodes, and other parameters affect sensitivity and resolution—some effects are in opposite directions. As in other analytical techniques, an improvement in resolution results in decreasing sensitivity.

The present embodiments utilize the two mobility spectrometry techniques described herein in parallel to take advantage of separation or resolution capabilities of both. Resolution of each of the techniques is maintained and there are no ion losses between the spectrometers. The detectors acting together as a "fused" sensor provide analytical chemical power for successful detection and identification of, for example, unknown bulk explosives (UBE) and homemade explosives (HME) in addition to detection of CW agents, TICs/TIMs, NTA, explosives and other dangerous materials. Sensitivity and response time are comparable.

Referring to exemplary configurations of the fused IMS and DIMS sensor technologies shown in FIGS. 4 through 11, in order to realize the full advantages of fusing the complementary aspects of the two technologies, the IMS and DIMS cells are such that a single ionization source and an ion-molecule reaction single reaction region is common to both. Exemplary DIMS cells which may be modified for use with the present embodiments are described in U.S. Pat. Nos. 8,146,404, 7,576,322 and 7,579,589. Taking advantage of common components allows for reduced footprint and implementation through a hand-held device.

Figure 4:
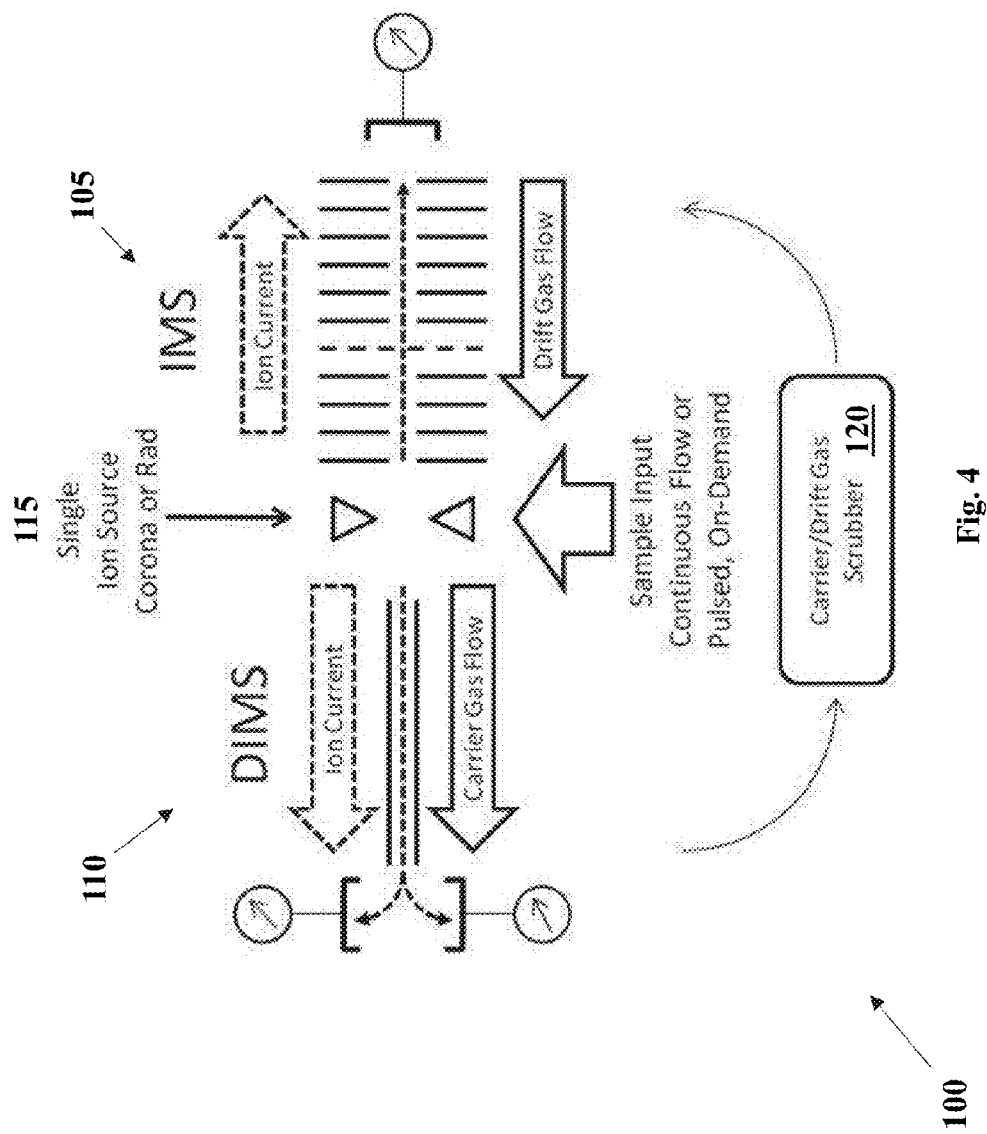
FIG. 4 is a schematic showing a hybrid IMS-DIMS system in accordance with an embodiment herein.
Figure 5:
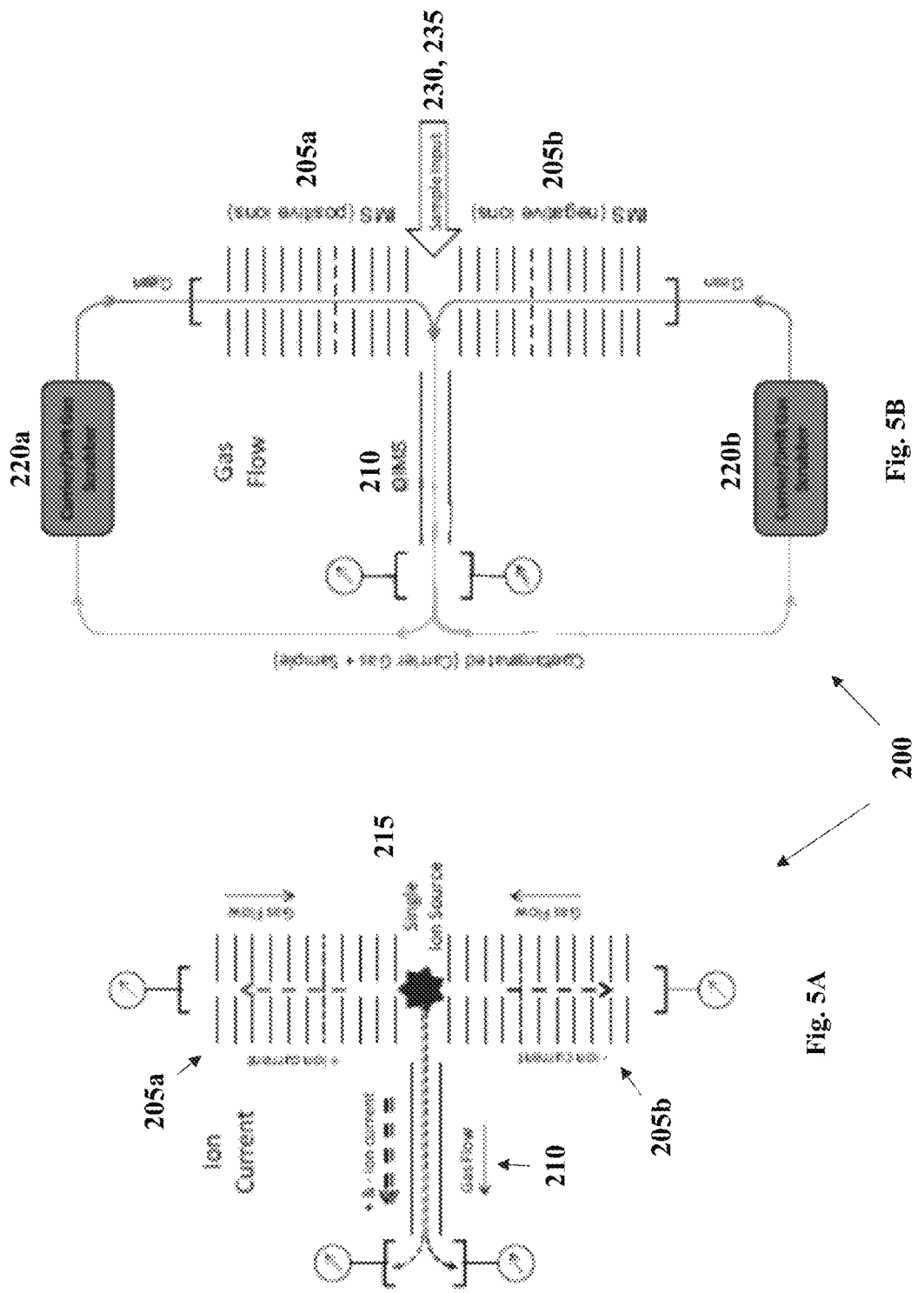
FIGS. 5a and 5b are schematics showing a hybrid IMS-DIMS system having two IMS cells and scrubber configuration in accordance with an embodiment herein.
Figure 6:
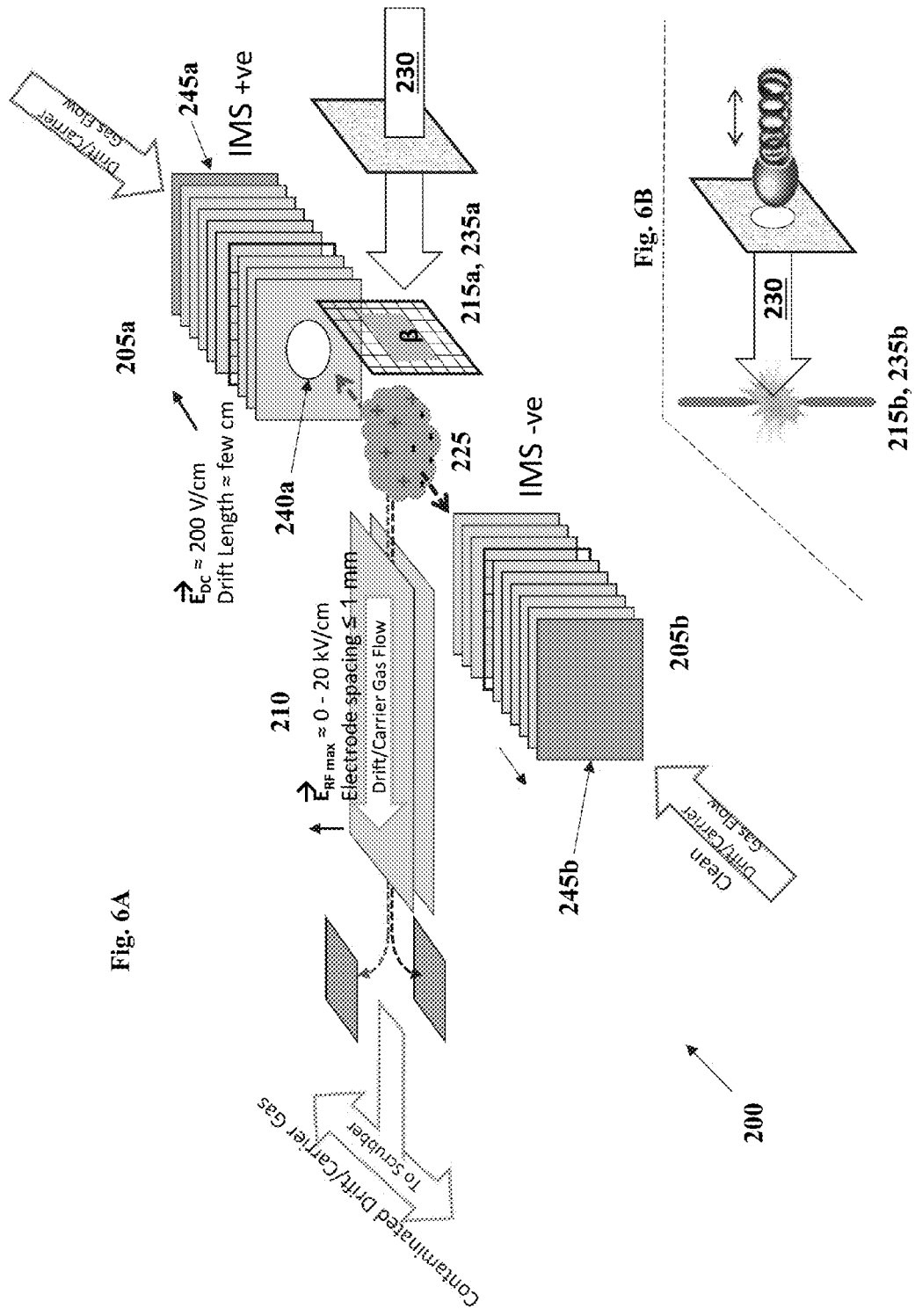
FIGS. 6a and 6b are schematics showing a more detailed schematic of FIG. 5a with differing ionization sources.

In a first embodiment shown in FIG. 4, the detector 100 includes a single IMS cell 105 to switch between positive and negative ion modes and a single DIMS cell 110. In the alternative embodiments of FIGS. 5 through 8, there are two IMS cells 205a and 205b, one positive and one negative to a single DIMS 210 (the entire detector system 200 being referred to as IMSx2). The internal gas flow requirement of IMS and DIMS detector cells lends itself to the illustrated configurations. The IMS process requires that a drift gas flow in the opposite direction of the ion current while DIMS requires that this carrier gas flow is in the same direction as the ion current. In FIG. 4, the drift gas in the IMS becomes the carrier gas in the DIMS. A single ion source 115 will serve to initiate the necessary ion-molecule chemistry for both cells. A single gas scrubber 120 will suffice for both cells.

In FIGS. 5a and 5b, the IMSx2 system 200 includes two IMS cells 205a and 205b, one positive and one negative, and a single DIMS 210 as well as dual scrubbers 220a, 220b. The IMSx2 system 200 is able to operate using a single ion source 215 for all three cells. Alternatively, a dual ion source configuration is also contemplated by one or more embodiments. Similarly, FIGS. 6a and 7 also illustrate IMSx2 system 200 including two IMS cells 205a and 205b, one positive and one negative, a single DIMS 210 and a single ion source 215. In the ionization space 225 in the vicinity of the single ion source 215, "primary" ions are formed as a result of electric discharge or ionizing radiation. The single ion source may be optimized in accordance with other system parameters and intended use for the system and may include, but is not limited to, corona discharge, atmospheric pressure photoionization (APPI), electrospray ionization (ESI), a radioactive source, laser-induced discharge and MALDI (matrix-assisted laser-desorption ionization). An analyte sample 230 is introduced to the system 200 through an inlet 235 and directed to ionization space 225. The characteristics of the inlet 235 vary in accordance with the type of ion source as highlighted further below and in the figures.

Figure 7:
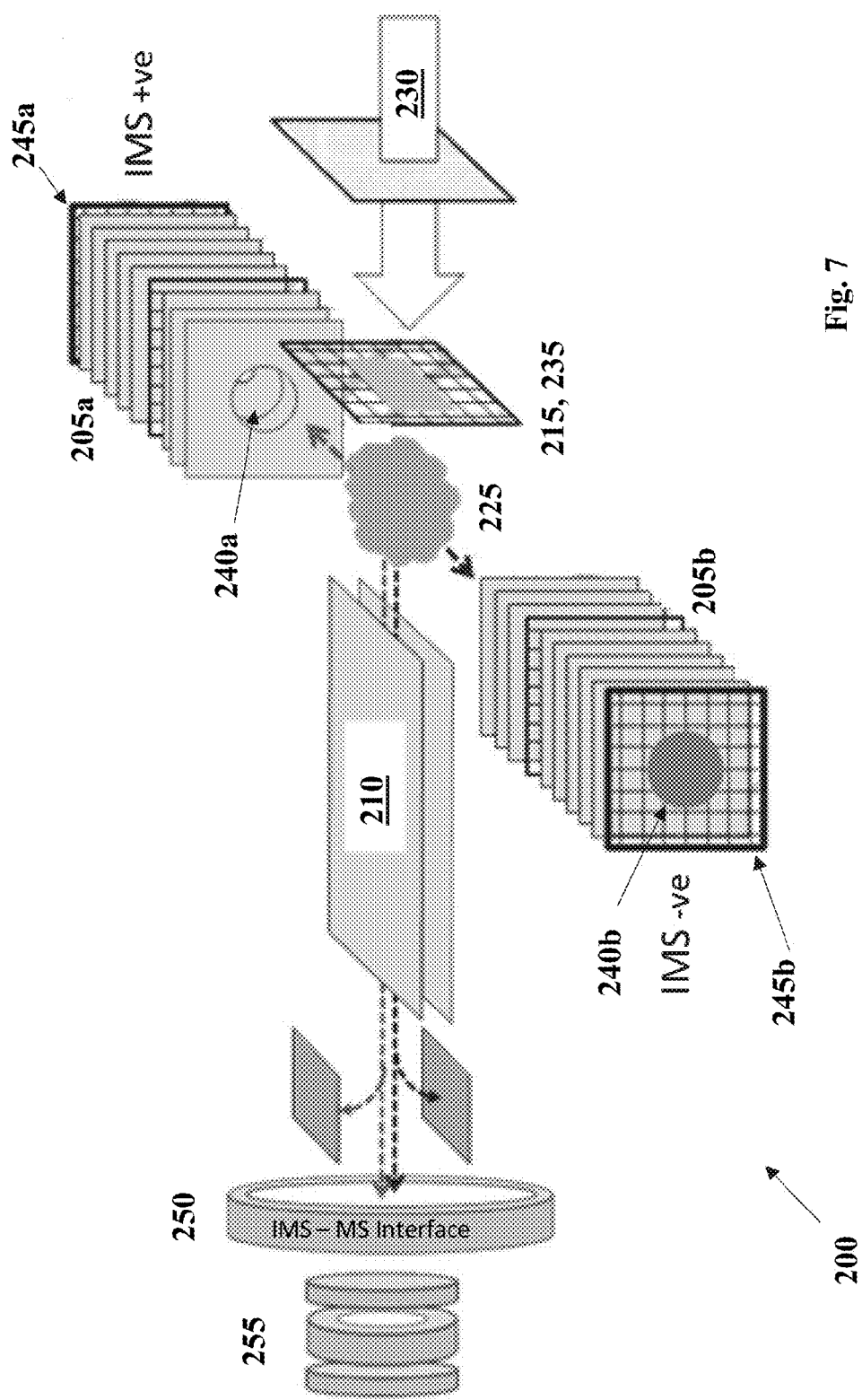
FIG. 7 is a schematic showing a hybrid IMSx2 mass spectrometer system in accordance with an embodiment herein.

Further to FIGS. 6a, 6b and 7, the inlet 235 configuration may vary in accordance with the configuration of the ionization source 215. That is, depending on the type of ionization source 215 that is utilized, the inlet 235 may be a membrane configuration 235a as shown in FIG. 6a when the ion source 215 is a radiation ion source 215a or the inlet 235 may be a pulsed inlet 235b as shown in FIG. 6b when the ion source 215 is a corona discharge source 215b. The individual IMS cells 205a and 205b receive respective positive and negative ions from the ionization space 225 into drift chambers or tubes 240a, 240b (not shown) and detection occurs at detectors 245a, 245b located at the opposite ends of the drift tubes 240a, 240b.

The configuration of the ion source 215 and ionization space 225 may be any configuration that allows for dual polarity ionization of the analyte sample. For example, the dual mode ion configuration described in U.S. Pat. No. 7,259,369 to Scott et al. or a variation thereof as contemplated by one skilled in the art may be utilized. U.S. Pat. No. 7,259,369 is incorporated herein by reference in its entirety. In a particular embodiment, the ion source 215 includes positive and negative DC corona ionization in ionization space 225. Additional structural details and dimensions of the ionization space (or chamber) 225 are discussed further below and illustrated in various figures.

The drift chambers or tubes 240a, 240b of the individual IMS cells 205a and 205b are integrated with the ionization space 225 in any configuration which facilitates the detection of both positively and negatively charged ions produced from a common source. Exemplary configurations are described in, by way of example, U.S. Pat. No. 4,445,038 to Spangler et al., U.S. Pat. No. 5,543,331 to Puumalainen and U.S. Pat. No. 7,576,321 to Wu which are incorporated herein by reference in their entireties. Individual IMS cells such as those embodied in the Excellims HPIMS products are exemplary of the components and operational characteristics which are contemplated for use as the cells 205a and 205b of the present embodiments. For exemplary purposes, the drift current (EDC) through the drift tubes which are on the order of a few centimeters in length is measured to be approximately 200 V/cm. The RF voltage amplitude ($E_{RF}$ max) in the DIMS component is in the approximate range of 0-20 kV/cm with an electrode spacing of ≤1 mm.

FIG. 7 illustrates yet another embodiment which is an IMSx2—Mass Spectrometry hybrid. DIMS, also known as FAIMS (Field Asymmetric Ion Mobility Spectrometry), interfaces 250 have been developed for mass spectrometers 255. One example is the FAIMS Interface for the Thermo Scientific series of mass spectrometers and another is the ultraFAIMS MS interface offered by Owlstone Nanotech. It is anticipated that real time responses result from the IMSx2 system with "good" specificity and "great" sensitivity. Responses with "good" sensitivity and "great" specificity are derived from the IMSx2-MS system with longer response times.

Figure 8A:
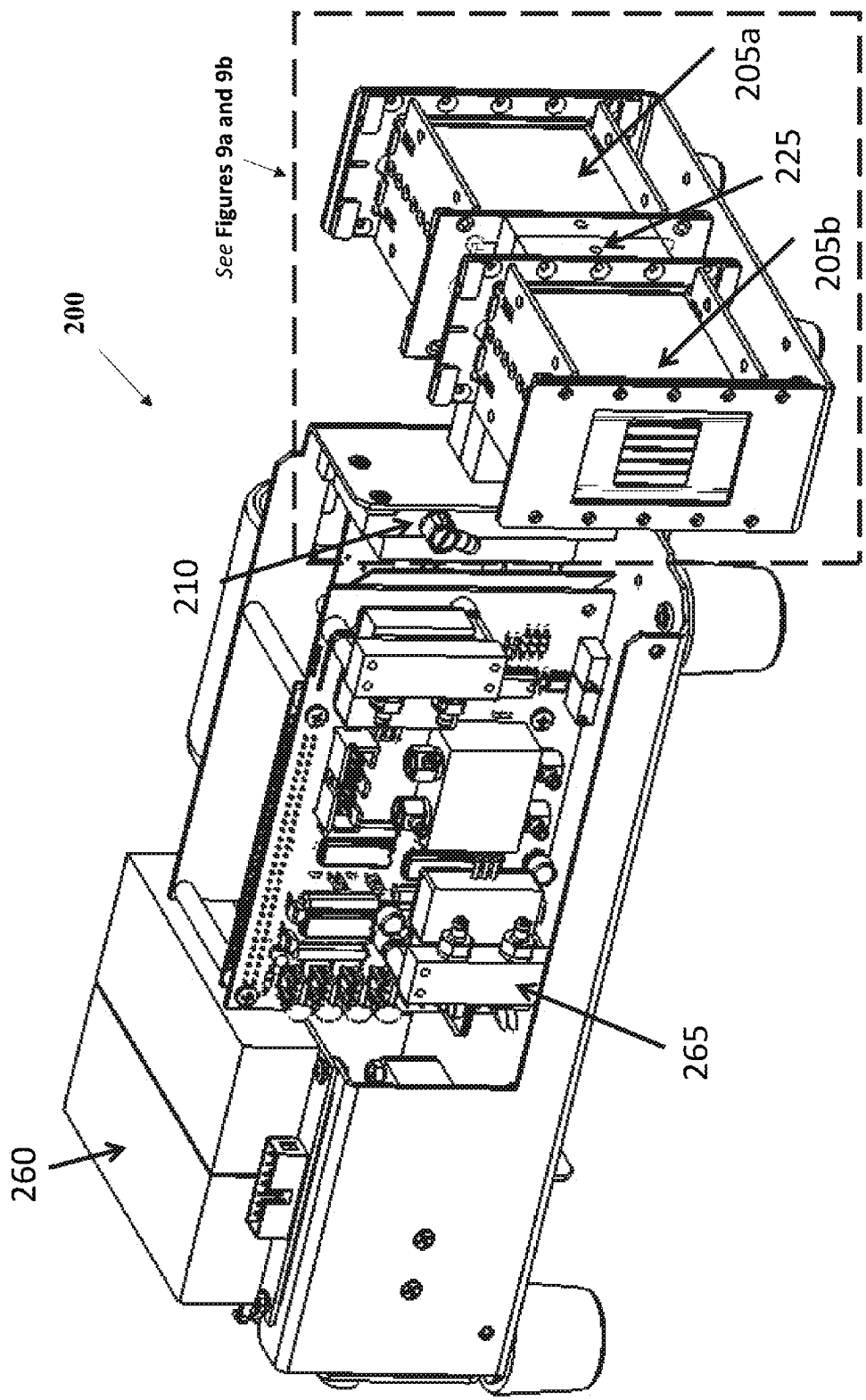
FIGS. 8a and 8b are isometric views of an IMSx2 system in accordance with embodiments described herein.
Figure 8B:
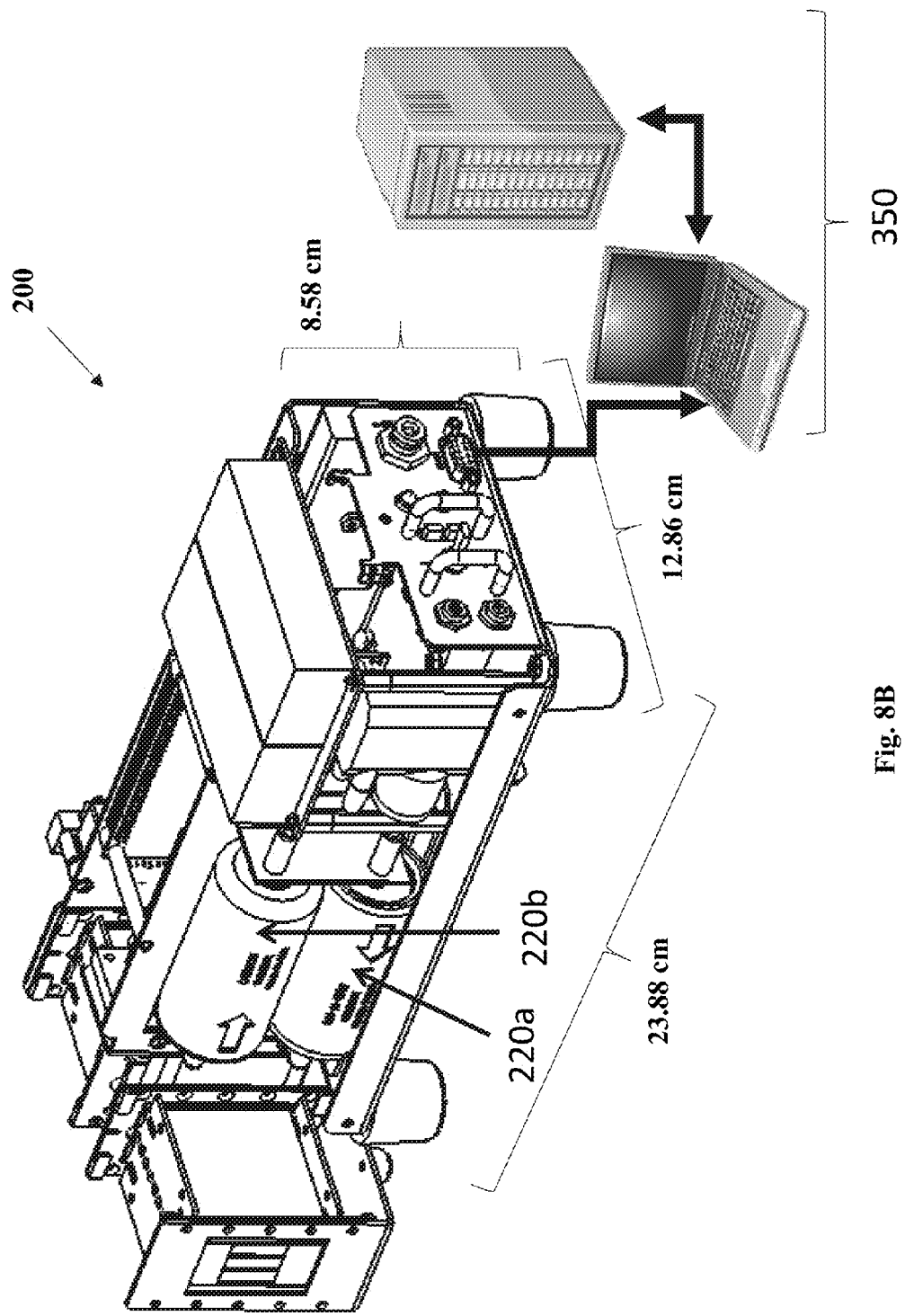

Referring to FIGS. 8a and 8b, an exemplary isometric view of an IMSx2 system configuration 200 in accordance with an embodiment is shown. As described above and shown in the view of FIG. 8a, the system includes a high voltage source 260, DIMS 210, ionization chamber 225, IMS sensor arrays 205a, 205b, and flow control components 265. In the second view shown in FIG. 8b, the carbon drift gas scrubbers 220a, 220b are shown. Additionally, FIG. 8b shows the system control panel, including on/off switch and, data port, the latter of which is critical to relaying sensor/detector data from the IMS cells and DIMS to the processing system 350, which includes fusion software for fusing the received data and making chemical detection determinations based thereon. For exemplary purposes, the dimensions of the power and control portion of the system are shown in FIG. 8b (the DIMS, IMS and ionization chamber component dimensions are discussed below and in later Figures). These dimensions 23.88 cm (L), 12.86 cm (W), and 8.56 cm (H) are exemplary and one skilled in the art recognizes variations in the dimensions in order to balance multiple factors including weight, footprint, mobility and results for the intended purpose and use.

The processing system 350 as illustrated is merely intended to be exemplary. One skilled in the art recognizes that there are numerous possible configurations and implementations for relaying data, i.e., the data port, and processing data. For example, the data port could be a wireless transmitter or a wireless transceiver wherein processing is completed remotely and results thereof are received back at the system and displayed to the user on a visual or audio display mounted on the system 200. Alternatively, the system 200 could include the processing system 350 within its footprint using, e.g., microprocessing technology on-board. In combination with a visual, auditory or tactile display mounted on the system 200, the system 200 is a stand-alone system and, as discussed below, may be constructed so as to be hand-held.

Figure 9A:
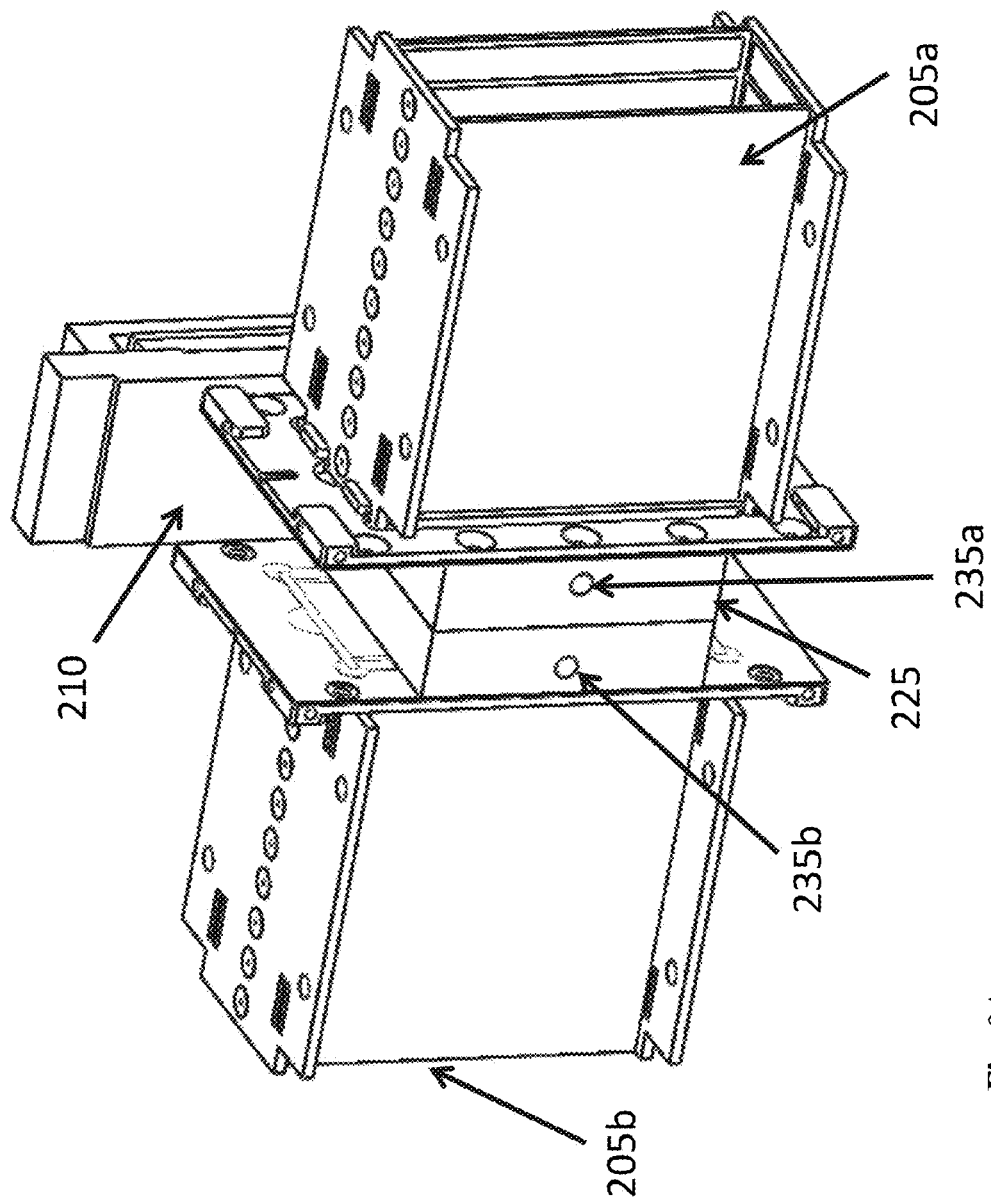
FIGS. 9a-9f provide views with exemplary dimensional information for key components of the IMSx2 system.
Figure 9B:
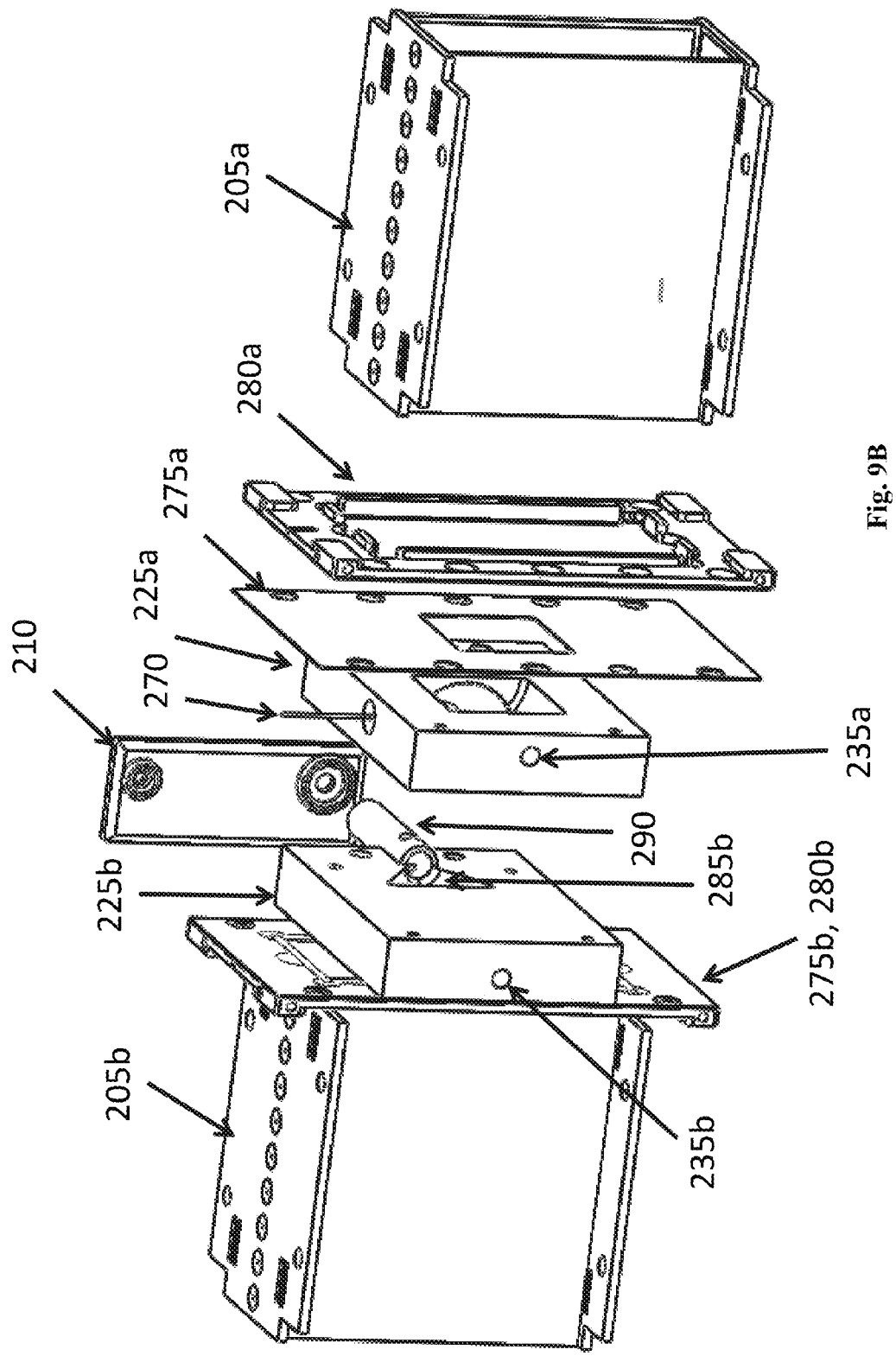

FIGS. 9a to 9e provide more detailed views of the configuration and integration of the IMS cells 205a, 205b, DIMS 210 and ionization chamber 225 components indicated by the dotted box in FIG. 8a. The exploded view in FIG. 9b shows the DIMS 210 in relation to the ionization chamber 225 which, in this particular embodiment, includes the corona needle 270 and is formed of two halves, 225a and 225b as shown with inlet ports 235a, 235b (alternatively, a single inlet port is acceptable). Each half of the ionization chamber includes a gasket 275a, 275b and bracket 280a, 280b for attaching to a respective IMS sensor arrays 205a, 205b. On the DIMS facing side of each half of the ionization chamber 225, there is a partial DIMS outlet 285b (only one is shown) which form a full DIMS outlet (not shown) for engaging with the DIMS ion inlet 290. Alternatively, the entirety of the DIMS outlet may be contained in a single half of the ionization chamber.

Figure 9C:
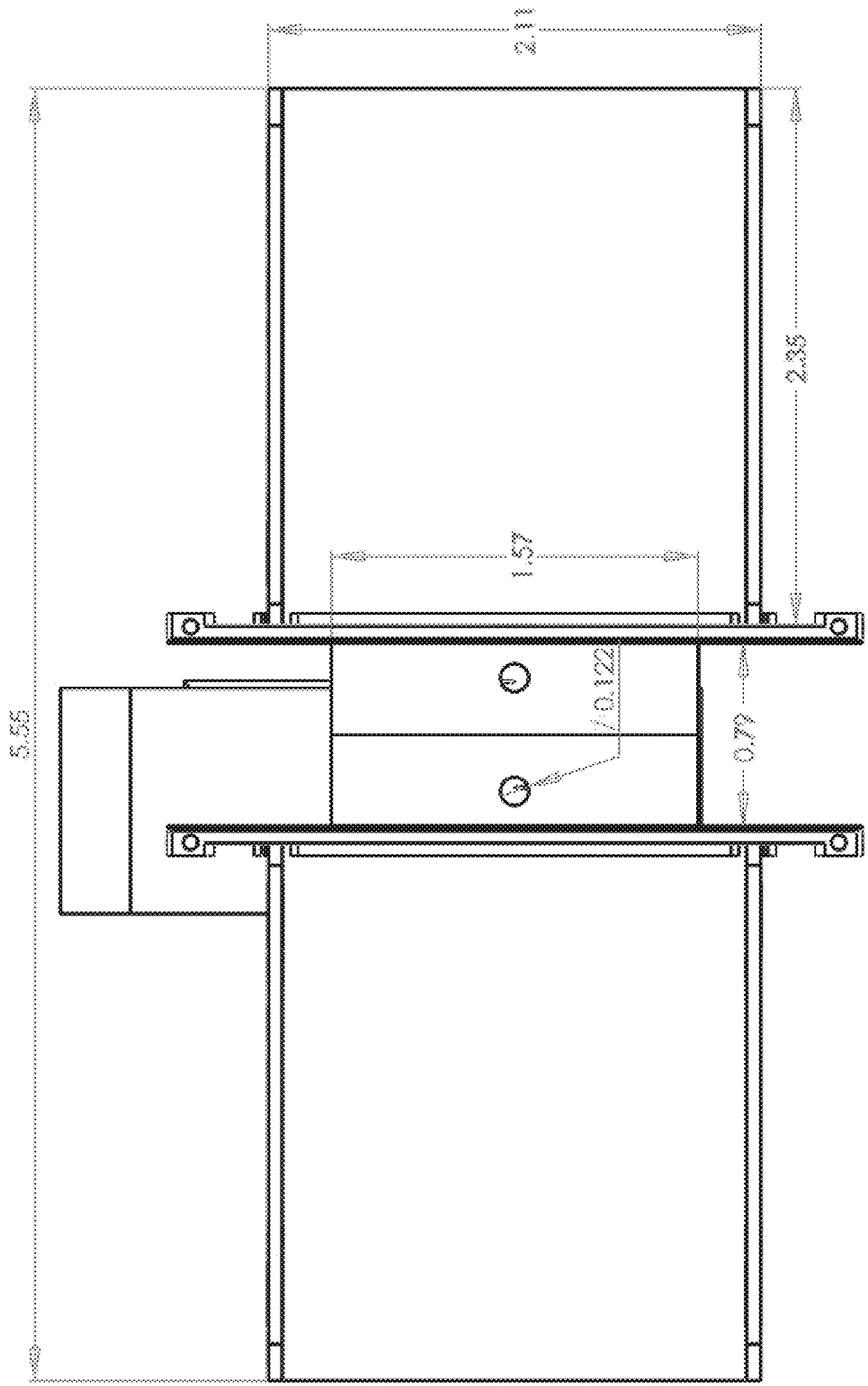
Figure 9D:
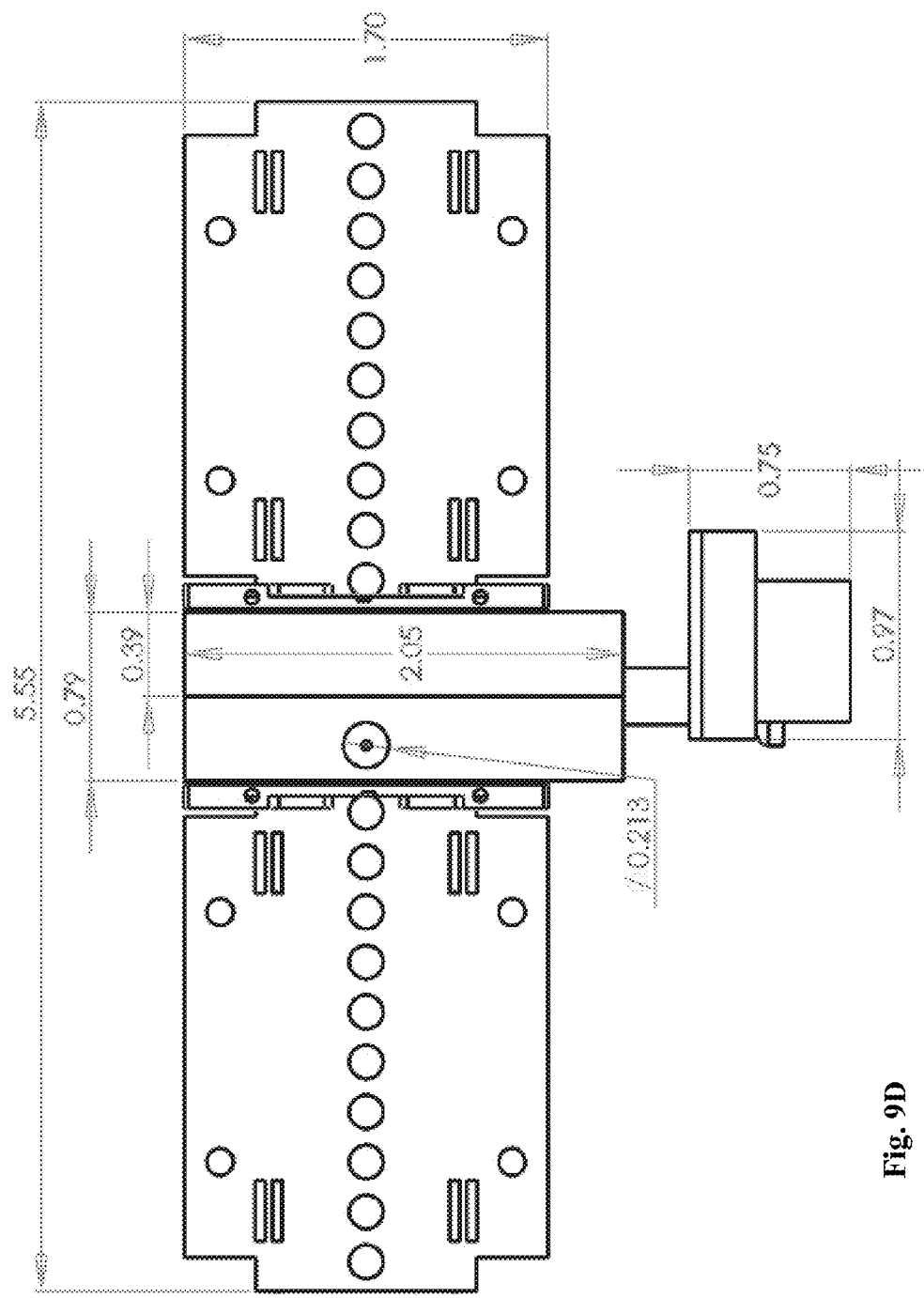
Figure 9E:
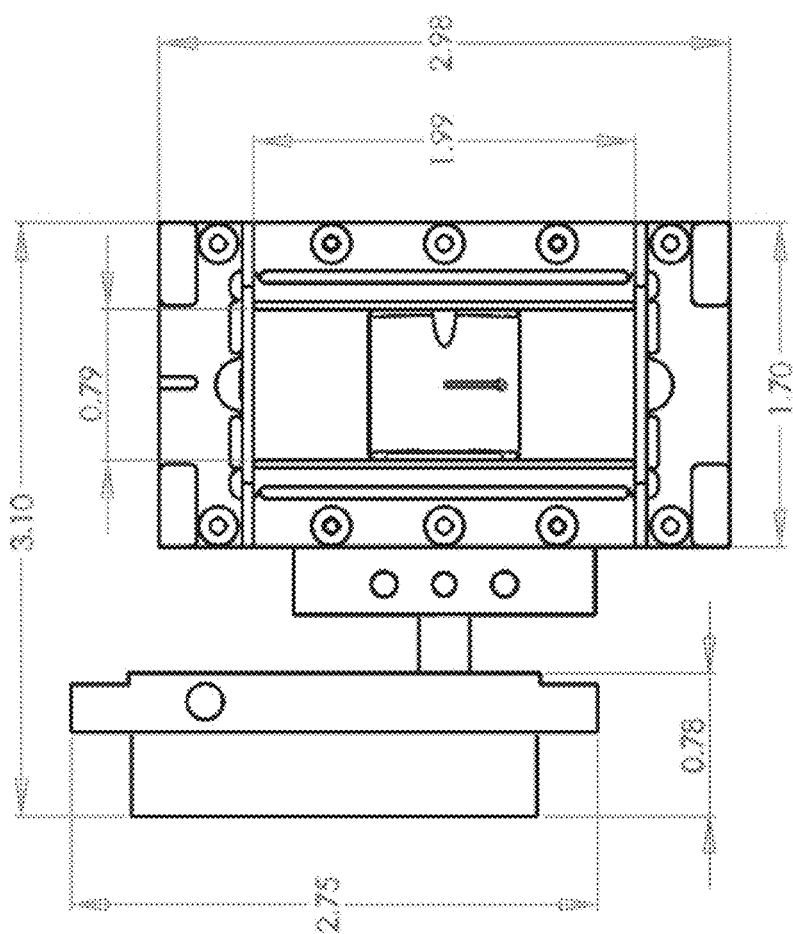

FIGS. 9c through 9e provide front, top and right side views with exemplary dimensional information. These dimensions, in centimeters, are provided for exemplary purposes and are not intended to limit the scope of the embodiments. One skilled in the art appreciates that variance in the dimensions are expected and would still be considered to be within the scope of the invention.

Figure 9F:
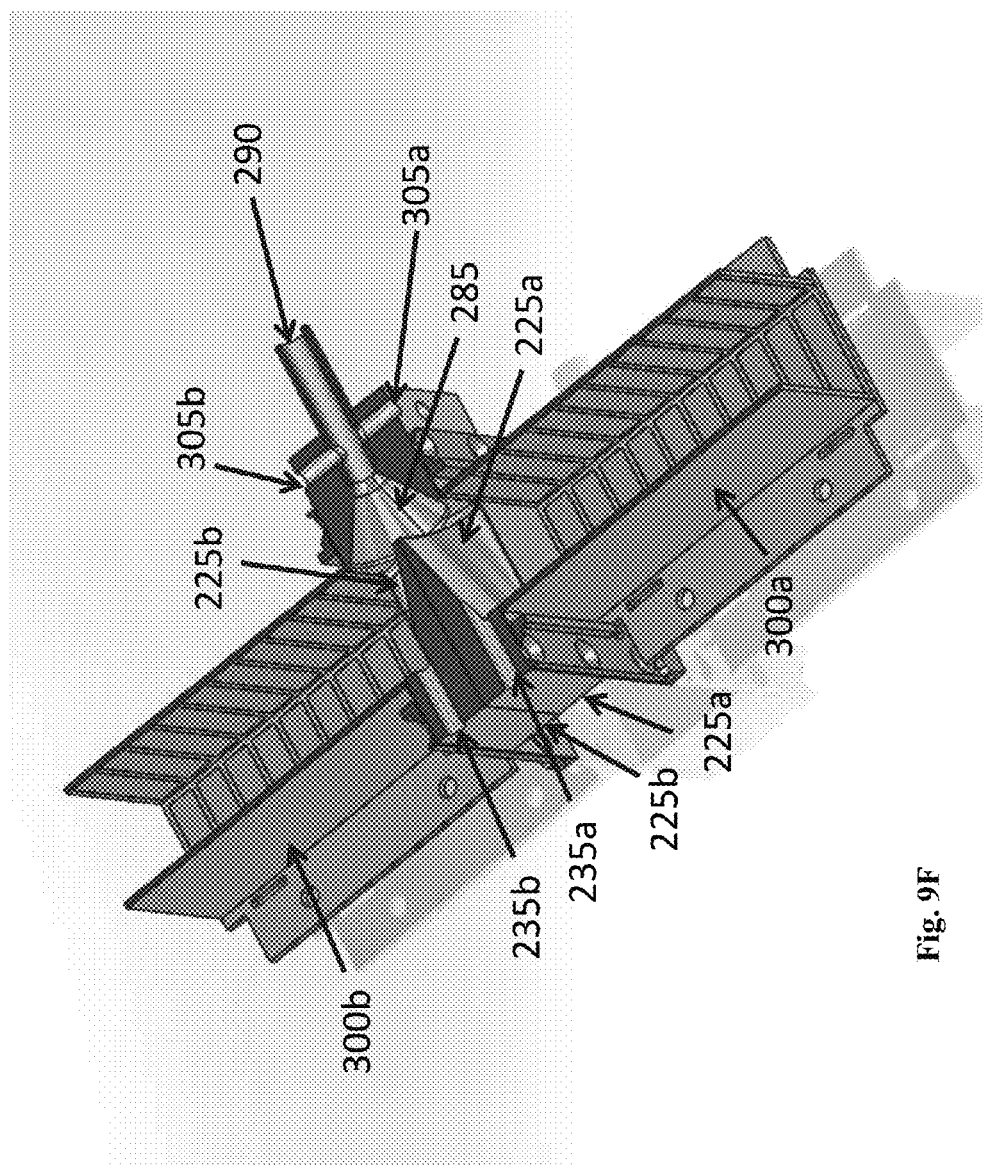

And FIG. 9f provides an additional cutaway view showing two halves 225a and 225b of the ionization chamber with sample inlet ports 235a, 235b, IMS outlets 300a, 300b, IMS sensor arrays 205a, 205b, DIMS outlet 285, DIMS ion inlet 290 and pre-DIMS drift gas bleed-off outlets 305a, 305b. The pre-DIMS drift gas bleed-off outlets are not a required feature.

FIGS. 10a and 10b provide comprehensive views of an ionization chamber 225 which, in this particular embodiment is formed of two halves, 225a and 225b and includes corona entry point 295, sample inlet ports 235a, 235b (alternatively, a single inlet port may be used), DIMS outlet 285, respective IMS outlets 300a, 300b and a pre-DIMS drift gas bleed-off outlet 305.

Figures 11A, 11B:
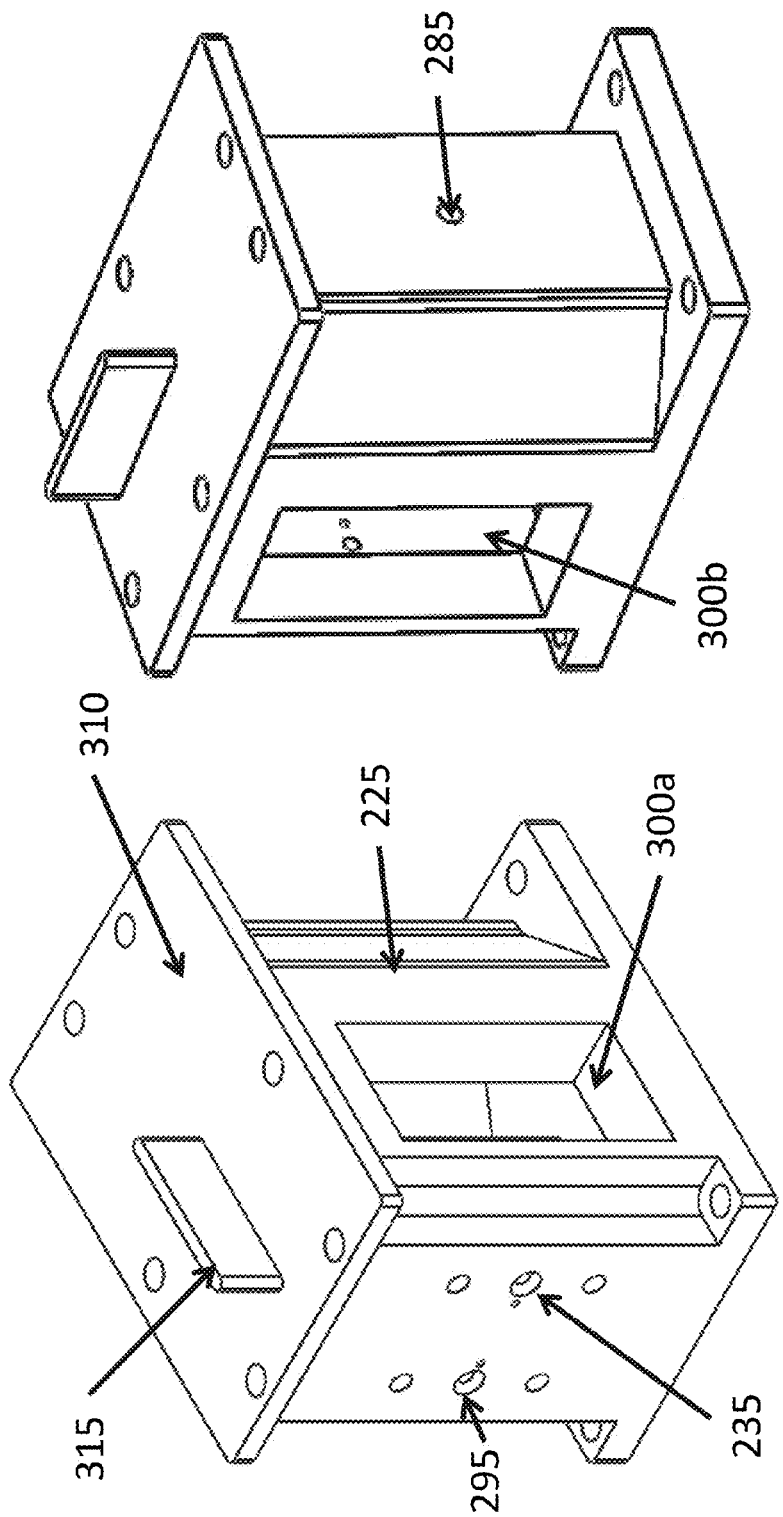
FIGS. 11a and 11b are isometric views of a first exemplary ionization chamber for use in the IMSx2 system described herein.

FIGS. 11a and 11b provide comprehensive views of an alternative ionization chamber 225 which, in this particular embodiment is a single component with an added top plate 310 and includes corona entry point 295, sample inlet port 235, DIMS outlet 285, respective IMS outlets 300a, 300b and an ion insulation shield 315.

During operation, additional exemplary metrics for the detection process include rate of drift gas supply, rate of gas bleed-off and rate supplied to DIMS. In a non-limiting implementation, values were determined to be 1 L/min drift gas supply and exhaust and 290 cc/min to DIMS. One skilled in the art also recognizes that other operational characteristics of the individual components are controllable to achieve desired results, including flow rates, currents/voltages, sensor/detector temperatures and the like.

The fused detector described herein is able to detect chemicals in all states of matter in the air and on surfaces, including land, personnel, equipment and facilities. The varied capabilities included in a single detector using some common components allows for reduced size, weight and power requirements, resulting in a single device that may be used in the field. Additionally, the dual and parallel signal processing with back end discriminatory processing, results in better sensitivity, reduced interference and minimization of false alarms. Such fields including, but not limited to, combat, anti-terrorism, law enforcement and the like. Specific applications include, but are not limited to, site assessment for chemical hazards, site exploitation, decontamination screening and clearance, autonomous detection in near real-time whole moving (e.g., on soldier, police, ship, other vehicles), outdoor and indoor monitoring for chemical hazards.

In concluding the detailed description, it should be noted that it would be obvious to those skilled in the art that many variations and modifications can be made to the embodiments without substantially departing from the principles described herein. Also, such variations and modifications are intended to be included herein within the scope as set forth in the appended claims.

It should be emphasized that the above-described embodiments are merely possible examples of the implementations, merely set forth for a clear understanding of the principles of thereof. Any variations and modifications may be made to the above-described embodiments of without departing substantially from the spirit of the principles of the embodiments. All such modifications and variations are intended to be included herein within the scope of the disclosure.

The present invention has been described in sufficient detail with a certain degree of particularity. The utilities thereof are appreciated by those skilled in the art. It is understood to those skilled in the art that the present disclosure of embodiments has been made by way of examples only and that numerous changes in the arrangement and combination of parts may be resorted without departing from the spirit and scope thereof.

We claim:

1. A chemical agent detector comprising:
   an ionization chamber including at least one ion source for generating positive and negative ions from a sample;
   a first ion mobility spectrometry cell integrated with the ionization chamber for receiving at least a first portion of the positive ions therefrom;
   a second ion mobility spectrometry cell integrated with the ionization chamber for receiving at least a first portion of the negative ions therefrom;
   a differential ion mobility spectrometry cell integrated with the ionization chamber for receiving at least a second portion of the positive ions and at least a second portion of the negative ions therefrom;
   the ionization chamber further including a front face;
   a back face opposite the front face;
   first and second side faces opposite one another and between, perpendicular to and connecting the front face and the back face;
   a top face perpendicular to and connecting the front face, back face and first and second side faces:
   wherein the front face includes at least one input port for receiving the sample into the ionization chamber, the top face includes at least one input port for receiving the ion source, the first side face includes an i/o port for passing the first portion of positive ions to the first ion mobility spectrometry cell and receiving a first IMS drift gas into the ionization chamber from the first ion mobility spectrometry cell, the second side face includes an i/o port for passing the first portion of negative ions to the second ion mobility spectrometry cell and receiving a second IMS drift gas into the ionization chamber from the second mobility spectrometry cell, and the back face includes and an exit port for passing the second portion of positive ions, the second portion of negative ions and a carrier gas consisting of the first and second IMS drift gases to the differential ion mobility spectrometry cell; and
   a processor for separately receiving first detection data from the first ion mobility spectrometry cell, second data from the second ion mobility spectrometry cell, and third data from the differential ion mobility spectrometry cell and processing the first, second and third detection data to determine presence of one or more chemical agents in the sample.

2. The chemical agent detector according to claim 1, wherein the exit port to the differential ion mobility spectrometry cell further includes at least one side port for allowing a first portion of the carrier gas to exit prior to entering the differential ion mobility spectrometry cell.

3. The chemical agent detector according to claim 2, further comprising first and second gas scrubbers for receiving a second portion of the carrier gas after it has passed through the differential ion mobility spectrometry cell and the first portion of the carrier gas from the at least one side port, removing contaminants therefrom and returning a clean drift gas to the first and second ion mobility spectrometry cells, wherein the clean drift gas flows in an opposite direction to the first portion of positive ions and the first portion of negative ions flowing in the first and second ion mobility spectrometry cells.

4. The chemical agent detector according to claim 2, wherein there are two side ports for allowing a first portion of the carrier gas to exit prior to entering the differential ion mobility spectrometry cell.

5. The chemical agent detector according to claim 1, wherein the ion source is a corona discharge source.

6. The chemical agent detector according to claim 1, further comprising a mass spectrometer interfaced with an output of the differential ion mobility spectrometry cell.

7. The chemical agent detector according to claim 1, wherein the at least one ion source is a single ion source.

8. The chemical agent detector according to claim 1, further comprising an indicator selected from the group consisting of audio, visual and tactile indicators for indicating when the sample contains one or more predetermined chemical agents.

9. A hand-held chemical agent detector comprising:
   an ionization chamber including at least one ion source for generating positive and negative ions from a sample, wherein the dimensions of the ionization chamber are less than 1 cm width, 2.5 cm length and 2.0 cm height;
   a first and second ion mobility spectrometry cells integrated with the ionization chamber for receiving at least a first portion of the positive and negative ions therefrom, wherein the dimensions of the first and second ion mobility spectrometry cells are less than 2.5 cm width, 2.0 cm length and 2.5 cm height; and
   a differential ion mobility spectrometry cell integrated with the ionization chamber for receiving at least a second portion of the positive ions and at least a second portion of the negative ions therefrom, wherein the dimensions of the differential ion mobility spectrometry cell are less than 1 cm width, 1.0 cm length and 3.0 cm height,
   the ionization chamber further including:
   a front face;
   a back face opposite the front face;
   first and second side faces opposite one another and between, perpendicular to and connecting the front face and the back face;
   a top face perpendicular to and connecting the front face, back face and first and second side faces;
   wherein the front face includes at least one input port for receiving the sample into the ionization chamber, the top face includes at least one input port for receiving the ion source, the first side face includes an i/o port for passing the first portion of positive ions to the first ion mobility spectrometry cell and receiving a first IMS drift gas into the ionization chamber from the first ion mobility spectrometry cell, the second side face includes an i/o port for passing the first portion of negative ions to the second ion mobility spectrometry cell and receiving a second IMS drift gas into the ionization chamber from the second mobility spectrometry cell, and the back face includes and an exit port for passing the second portion of positive ions, the second portion of negative ions and a carrier gas consisting of the first and second IMS drift gases to the differential ion mobility spectrometry cell.

10. The hand-held chemical agent detector according to claim 9, wherein the exit port to the differential ion mobility spectrometry cell further includes at least one side port for allowing a first portion of the carrier gas to exit prior to entering the differential ion mobility spectrometry cell.

11. The handle-held chemical agent detector according to claim 10, further comprising first and second gas scrubbers for receiving a second portion of the carrier gas after it has passed through the differential ion mobility spectrometry cell and the first portion of the carrier gas from at least one side port, removing contaminants therefrom and returning a clean drift gas to the first and second ion mobility spectrometry cells, wherein the clean drift gas flows in an opposite direction to the first portion of positive ions and the first portion of negative ions flowing in the first and second ion mobility spectrometry cells.

12. The hand-held chemical agent detector according to claim 9, wherein the at least one ion source is a single corona discharge source.

13. The hand-held chemical agent detector according to claim 9, further comprising two side ports located at an interface between the ionization chamber and the differential ion mobility spectrometry cell for allowing a first portion of the carrier gas to exit prior to entering the differential ion mobility spectrometry cell.

\* \* \* \* \*